United States Patent [19]

Marsh et al.

[11] 3,993,704

[45] Nov. 23, 1976

[54] PARA-NITROBENZOTRIBROMIDE PROCESS

[75] Inventors: Frank Dennis Marsh, Wilmington; Colin Leslie McIntosh, Newark, both of Del.

[73] Assignee: E. I. Du Pont de Nemours and Company, Wilmington, Del.

[22] Filed: Dec. 22, 1975

[21] Appl. No.: 643,391

[52] U.S. Cl. .............................................. 260/646
[51] Int. Cl.$^2$ ....................................... C07C 79/12
[58] Field of Search ................................... 260/646

[56] References Cited
UNITED STATES PATENTS
3,267,159   8/1966   Shipp ................................. 260/646

Primary Examiner—Leland A. Sebastian

[57] ABSTRACT

The conversion of p-nitrobenzal bromide to p-nitrobenzotribromide, an intermediate in the preparation of the insecticide, 1,5-bis(4-trifluoromethylphenyl)-3-cyanoformazan, by reacting p-nitrobenzal bromide with an alkali or alkaline earth metal hypobromite is improved by carrying out the reaction in a two-phase, water-organic solvent system.

7 Claims, No Drawings

PARA-NITROBENZOTRIBROMIDE PROCESS

BACKGROUND OF THE INVENTION

This invention relates to an improved process for the conversion of p-nitrobenzal bromide to p-nitrobenzotribromide. p-Nitrobenzotribromide is an intermediate to the insecticide, 1,5-bis(4-trifluoromethylphenyl)-3-cyanoformazan which is described in the German publication Offenlegungsschrift 2,460,255.

H. Fisher in Journal of American Chemical Society, 56, 2469 (1934) reports the conversion of p-nitrobenzal bromide to p-nitrobenzotribromide by reacting p-nitrobenzal bromide in a heterogeneous aqueous reaction medium with sodium hypobromite at 25° C for four days, which results in a 78% yield. R. G. Jones in *Journal of American Chemical Society*, 69, 2346 (1947) reports the same conversion on a larger scale according to the method of Fisher, but with a two-fold excess of sodium hypobromite.

Maginmity and Eisenmann in *Journal of American Chemical Society*, 74, 6119 (1952), Fukui in *Nippon Kagaku Zasshi*, 79, 899 (1958) [Chemical Abstract 54, 4430 (1958)] and South African Patent 68-06,020 (1969) also mention the preparation of p-nitrobenzotribromide from p-nitrobenzal bromide in an aqueous sodium hypobromite system.

SUMMARY OF THE INVENTION

This invention provides an improved method for conversion of p-nitrobenzal bromide to p-nitrobenzotribromide by reaction with an alkali or alkaline earth metal hypobromite such as sodium, potassium or calcium, the improvement being the use of a two-phase water-organic solvent system to give increased yield and higher purity in a greatly shortened reaction time.

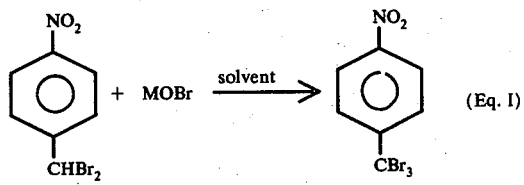

Suitable brominating agents will have a solubility in water (at 25° C) of at least 1% by weight. Suitable organic solvents for the second component of the water-organic solvent system are those organic solvents with the following characteristics:

a. immiscible with water;
b. inert to hypobromite under the operating conditions of this invention;
c. have a solubility for p-nitrobenzal bromide of at least 5% by weight.

DETAILED DESCRIPTION OF THE INVENTION p-Nitrobenzal bromide is a precursor to p-aminobenzotrifluoride used to prepare the insecticide, 1,5-bis(4-trifluoromethylphenyl)-3-cyanoformazan according to the reaction scheme below:

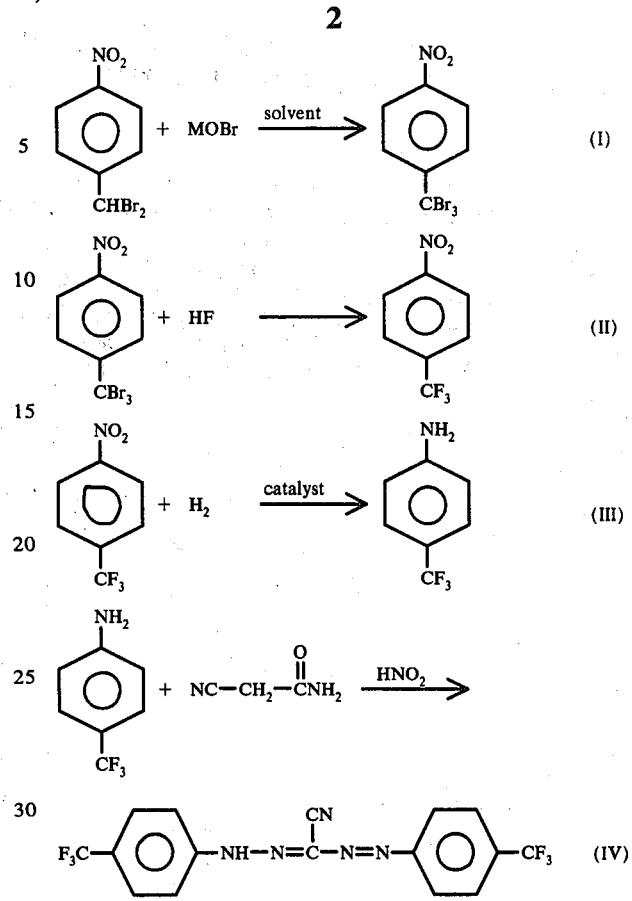

Equation (I) is the reaction improved by this invention and is a brominating step. The brominating agent employed is an alkali or an alkaline earth metal hypobromite such as sodium, potassium or calcium, which has a solubility in water (at 25° C) of at least 1% by weight. The required metal hypobromite is prepared by reaction of the metal hydroxide with bromine in an aqueous system according to the following equation, which is well known in the art.

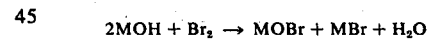

The solvent system for the reaction of equation I is a two-phase, water-organic system. The limitations were given in the Summary of the Invention, and suitable organic solvents include, but are not limited to, chlorinated hydrocarbons such as carbon tetrachloride, and aromatic hydrocarbons, optionally substituted with halogen or methyl groups such as toluene or chlorobenzene.

The ratio of water to organic solvent in the two-phase system can range from 10:1 to 1:10.

The reaction of equation I can be run at temperatures between 0° C and 100° C; it is preferred that the reaction be carried out between 25° C and 60° C, and most preferably between 40° C and 60° C.

The following examples illustrate the embodiments of this invention.

EXAMPLE 1

A solution of 51 parts of p-nitrobenzal bromide in 500 parts of carbon tetrachloride is added to a solution of 80 parts of bromine plus 160 parts of 50% sodium hydroxide in 2,000 parts of water at 50° C. The mixture is stirred with a mechanical stirrer for 2.5 hours. The carbon tetrachloride layer is separated, dried and evaporated to give 58 parts (90% yield) of p-nitrobenzotribromide, m.p. 81-3° C.

EXAMPLE 2

A solution of 100 parts of p-nitrobenzal bromide in 500 parts of toluene is added to a solution of 80 parts of bromine plus 160 parts of 50% sodium hydroxide in a 1,000 parts of water at 50° C. The mixture is stirred mechanically at 50° C for 10 hours. The toluene layer is separated; the water layer is extracted with 500 parts of toluene. The combined toluene layers are dried and evaporated to give 110 parts (85% yield) of p-nitrobenzotribromide, m.p. 74°-81° C.

EXAMPLE 3

A solution of 100 parts of p-nitrobenzal bromide in 1,000 parts of chlorobenzene is stirred with a solution of 80 parts of bromine plus 160 parts of 50% sodium hydroxide in 1,000 parts of water at 50° C for 10 hours. The bottom layer is separated and evaporated to dryness to give 110 parts (86% yield) of p-nitrobenzotribromide, m.p. 66°-70° C.

EXAMPLE 4

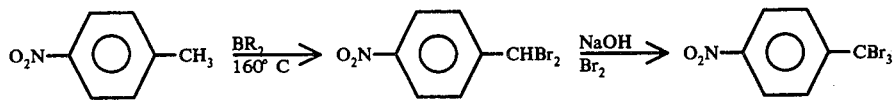

685 Parts of p-nitrotoluene is heated to 160° C and 2,050 parts of bromine is added over a 4-hour period at 160°-170° C. The mixture is cooled to 40° C and 2,000 parts of carbon tetrachloride is added. The carbon tetrachloride solution is added to a stirring solution containing 5,000 parts of water, 1,800 parts of 50% sodium hydroxide and 900 parts of bromine. The mixture is held at 50° C for 4 hours. The organic layer is separated, dried over anhydrous MgSO₄ and the solvent is removed under vacuum to give 1,623 parts (87% yield) of p-nitrobenzotribromide, m.p. 78°-81° C.

The following procedures illustrate the utility of p-nitrobenzotribromide as an intermediate to p-aminobenzotrifluoride.
Procedure 1:

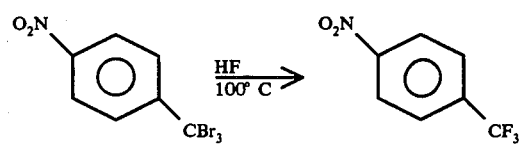

300 Parts of p-nitrobenzotribromide is placed in a pressure vessel. The vessel is charged with 350 parts of hydrogen fluoride and the resulting mixture is agitated at 100° C for 4 hours, then the excess hydrogen fluoride is removed under reduced pressure at 25° C. The contents of the vessel are transferred to a mixture of 500 parts of methylene chloride and 1,000 parts water, and sodium bicarbonate is added with stirring until the mixture reaches pH 7. The organic layer is separated, dried over MgSO₄ and the solvent is removed under reduced pressure to give 177 parts (99% yield) of p-nitrobenzotrifluoride.

Procedure 2:

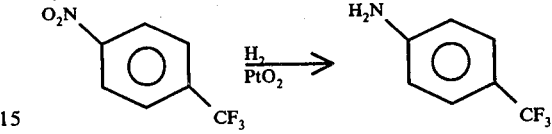

160 Parts of p-nitrobenzotrifluoride is dissolved in 500 parts of ethanol and 1 part platinum oxide catalyst is added. The mixture is placed in a pressure vessel and hydrogen is added at a temperature of 30° C and a pressure of 13.6 atmospheres. The hydrogen pressure is increased to 34 atmospheres during the course of the reaction, which continues until the hydrogen uptake ceases. The excess hydrogen is removed from the reaction vessel under reduced pressure and the catalyst is removed from the mixture by filtration. The solvent is removed from the filtrate under reduced pressure to give 127 parts (94% yield) of p-aminobenzotrifluoride.

We claim:
1. In the conversion of p-nitrobenzal bromide to p-nitrobenzotribromide, by reaction with an alkali or alkaline earth metal hypobromite, the improvement which comprises carrying out the reaction in a two-phase, water-organic solvent system.

2. The process of claim 1 wherein the organic solvent is immiscible with water, inert to hypobromite under the process conditions, and has a solubility for p-nitrobenzal bromide of at least 5% by weight.

3. The process of claim 2 wherein the water:organic ratio of the water-organic solvent is from 10:1 to 1:10.

4. The process of claim 3 wherein the organic solvent is selected from chlorinated hydrocarbons and aromatic hydrocarbons, optionally substituted with halogen or methyl groups.

5. The process of claim 3 wherein the organic solvent is selected from carbon tetrachloride, toluene and chlorobenzene.

6. The process of claim 3 wherein the brominating agent is selected from sodium, potassium, and calcium hypobromite; the organic solvent is selected from carbon tetrachloride, toluene, and chlorobenzene; and the temperature of the reaction is between 40°-60° C.

7. The process of claim 3 wherein the organic solvent is carbon tetrachloride.